US011111469B2

(12) United States Patent
Raimondi et al.

(10) Patent No.: US 11,111,469 B2
(45) Date of Patent: Sep. 7, 2021

(54) DEVICE FOR CELL CULTURE

(71) Applicant: POLITECNICO DI MILANO, Milan (IT)

(72) Inventors: Manuela Teresa Raimondi, Milan (IT); Matteo Lagana, Longone Al Segrino (IT)

(73) Assignee: POLITECNICO DI MILANO, Milan (IT)

( * ) Notice: Subject to any disclaimer, the term of this patent is extended or adjusted under 35 U.S.C. 154(b) by 373 days.

(21) Appl. No.: 16/302,157

(22) PCT Filed: May 5, 2017

(86) PCT No.: PCT/IB2017/052626
§ 371 (c)(1),
(2) Date: Nov. 16, 2018

(87) PCT Pub. No.: WO2017/199121
PCT Pub. Date: Nov. 23, 2017

(65) Prior Publication Data
US 2019/0144810 A1 May 16, 2019

(30) Foreign Application Priority Data
May 18, 2016 (IT) .......................... 102016000051015

(51) Int. Cl.
C12M 1/00 (2006.01)
C12M 1/32 (2006.01)
(Continued)

(52) U.S. Cl.
CPC ......... C12M 23/38 (2013.01); B01L 3/50853 (2013.01); C02F 1/008 (2013.01); C02F 1/76 (2013.01); C12M 23/12 (2013.01); C12M 23/22 (2013.01); C12M 23/46 (2013.01); C12M 29/10 (2013.01); B01L 2300/0822 (2013.01);
(Continued)

(58) Field of Classification Search
None
See application file for complete search history.

(56) References Cited

U.S. PATENT DOCUMENTS 7,851,204 B2    12/2010  Klein et al.
2006/0234370 A1 10/2006  Korpinen et al.
2015/0247112 A1* 9/2015  Orr .................. C12M 23/12
                                                   506/9

FOREIGN PATENT DOCUMENTS

WO    WO2013086509 A1    6/2013

* cited by examiner

Primary Examiner — Holly Kipouros
(74) Attorney, Agent, or Firm — Dickinson Wright PLLC; Andrew D. Dorisio

(57) ABSTRACT

A device for cell culture comprising: a main body (11); said main body (11) comprises a plurality of circular portions (21-23); said device comprises a plurality of caps (51-53); each of said plurality of caps (51-53) comprises a base structure (58) having a circular hole (57), housing an upper slide (54) and an elastomeric layer (56) secured to said slide (54); said elastomeric layer (56) has a rectangular hole (59); said plurality of caps (51-53) being adapted to cooperate with said plurality of circular portions (21-23); each of said plurality of circular portions (21-23) each comprise an inlet hole (64-66) and an outlet hole (67-69) aligned with the long side of said rectangular hole (59), to perfuse the culture chamber (12-14) located in said rectangular hole (59) of said elastomeric layer (56).

10 Claims, 3 Drawing Sheets

Figure 1:
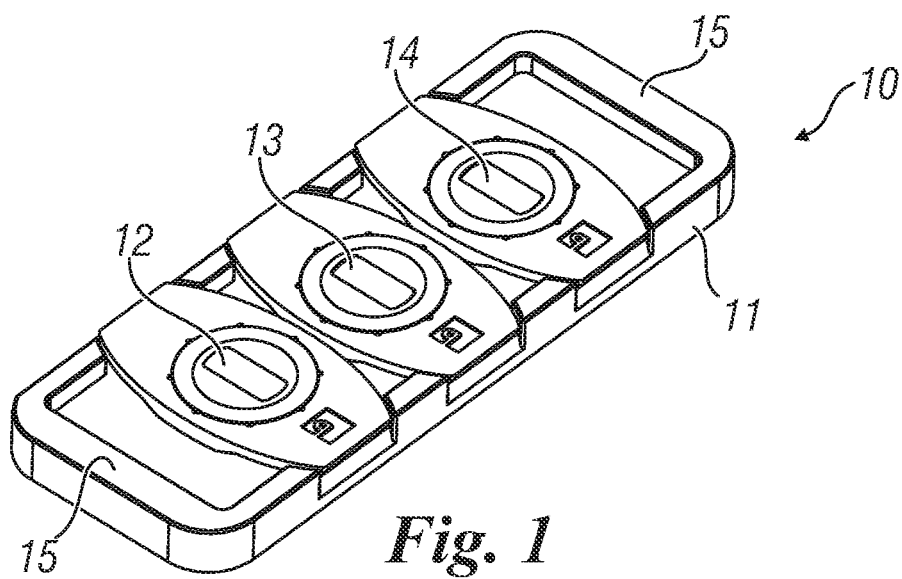

(51) Int. Cl.
    *B01L 3/00*           (2006.01)
    *C12M 3/00*         (2006.01)
    *C02F 1/00*          (2006.01)
    *C02F 1/76*          (2006.01)
    C02F 103/02      (2006.01)
    B63J 1/00         (2006.01)

(52) U.S. Cl.
    CPC ................ *B63J 1/00* (2013.01); *C02F 1/006* (2013.01); *C02F 2103/02* (2013.01); *C02F 2201/001* (2013.01); *C02F 2209/003* (2013.01); *C02F 2209/006* (2013.01); *C02F 2209/29* (2013.01); *C02F 2209/44* (2013.01); *C02F 2303/04* (2013.01); *C02F 2303/185* (2013.01); *C02F 2307/14* (2013.01)

DEVICE FOR CELL CULTURE

The present invention relates to a device for cell culture, more in particular to a modular bioreactor with separate chambers for microscopy.

TECHNICAL FIELD

As it is known, there are single bioreactors having a transparent portion to allow light to enter or to be able to view the cells.

BACKGROUND

The object of the present invention is that of providing a device for cell culture that allows viewing by means of a microscope without interrupting culture.

Another object is that of providing a device with several chambers perfused separately.

Yet another object is that of providing a device in which each chamber can be opened and closed repeatedly always maintaining the hydraulic seal.

In accordance with the present invention, these and other objects are achieved by a device for cell culture comprising: a main body; said main body comprises a plurality of circular portions; said device comprises a plurality of caps; each of said plurality of caps comprises a base structure having a circular hole, housing an upper slide and an elastomeric layer secured to said slide; said elastomeric layer has a rectangular hole; said plurality of caps being adapted to cooperate with said plurality of circular portions; each of said plurality of circular portions each comprise an inlet hole and an outlet hole aligned with the long side of said rectangular hole, to perfuse the culture chamber located in said rectangular hole of said elastomeric layer.

These objects are also achieved by a method for producing a device for cell culture according to claim 1, characterized in that it is produced by injection moulding.

SUMMARY

Further features of the invention are described in the dependent claims.

The advantages of this solution with respect to prior art solutions are numerous.

The device according to the present invention is optically accessible and allows inspection of the cell culture by means of standard or confocal optical microscopy, with white light, phase contrast or fluorescence. The optical accessibility allows the user of the device with any sensor, for example for measuring pH and for the concentration of solutes in a perfused solvent.

Moreover, the device is modular.

The geometry of the perfused culture chamber can house cell monolayers, cellular gels, three-dimensional scaffolds, or explanted or engineered portions of biological tissue.

Each of the perfused chambers is separated and isolated from the others as perfusion circuit, but can also be connected by means of bypass.

Each perfusion chamber has its own magnetic cover that can be operated independently of the other chambers.

The caps and the main body have a self-aligning geometry, so as to ensure immediate and correcting closure of the chambers during use.

The device is also inexpensive to produce through injection moulding of plastic materials and subsequent assembly by gluing, allowing them to be disposable despite being high performance.

BRIEF DESCRIPTION OF THE DRAWING FIGURES

Figure 2:
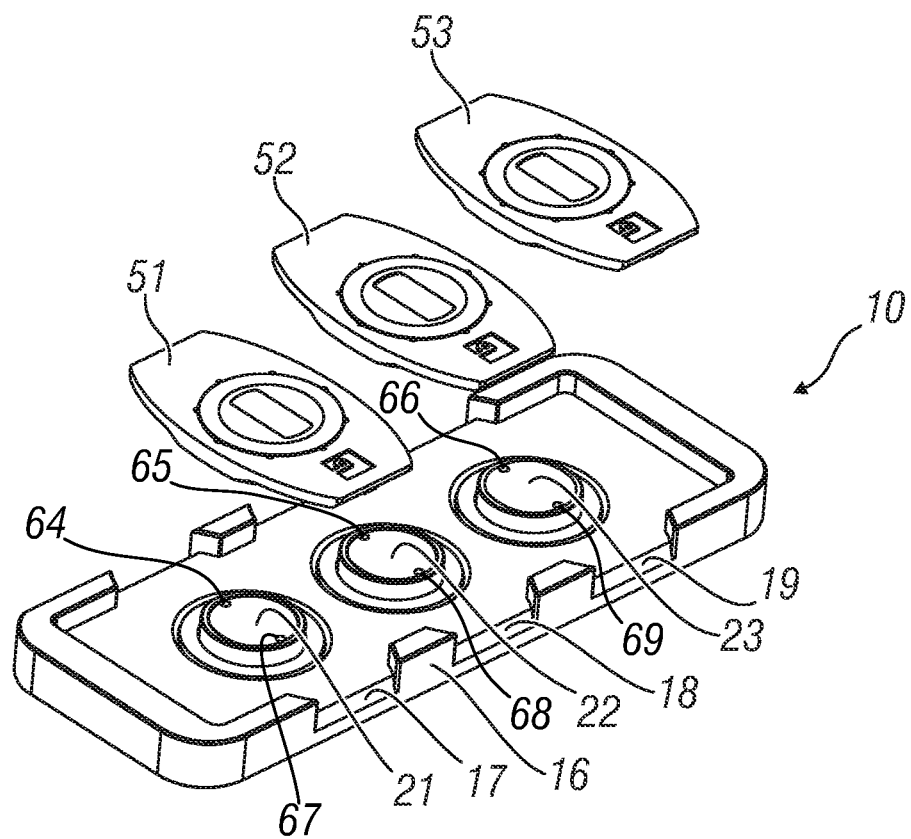
Figure 3:
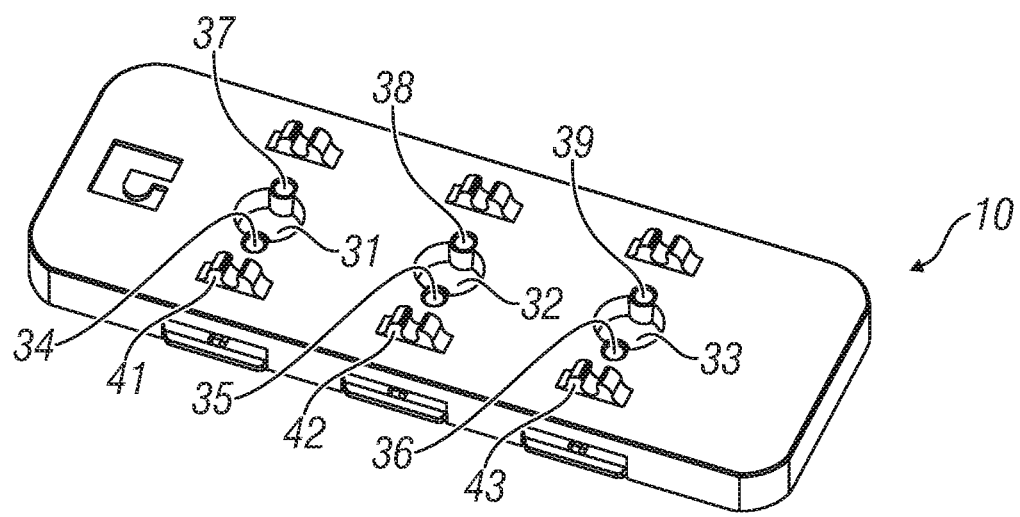
Figure 4:
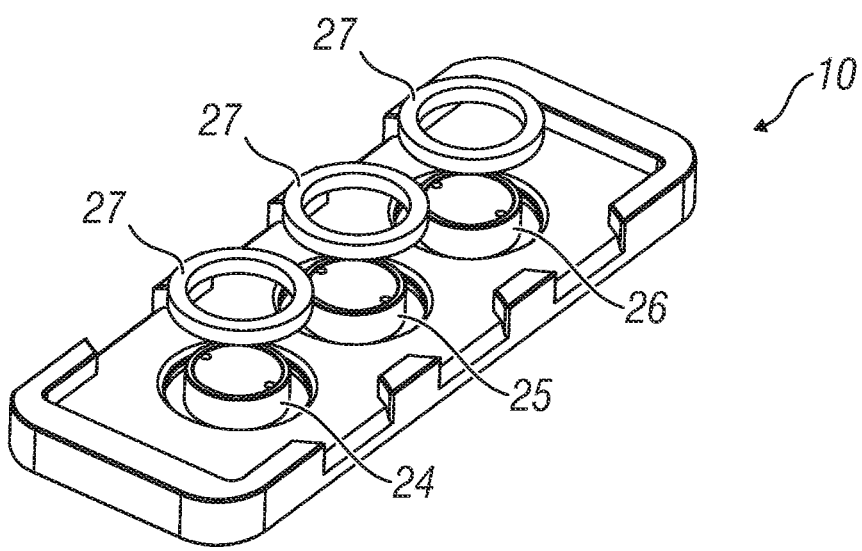
Figure 5:
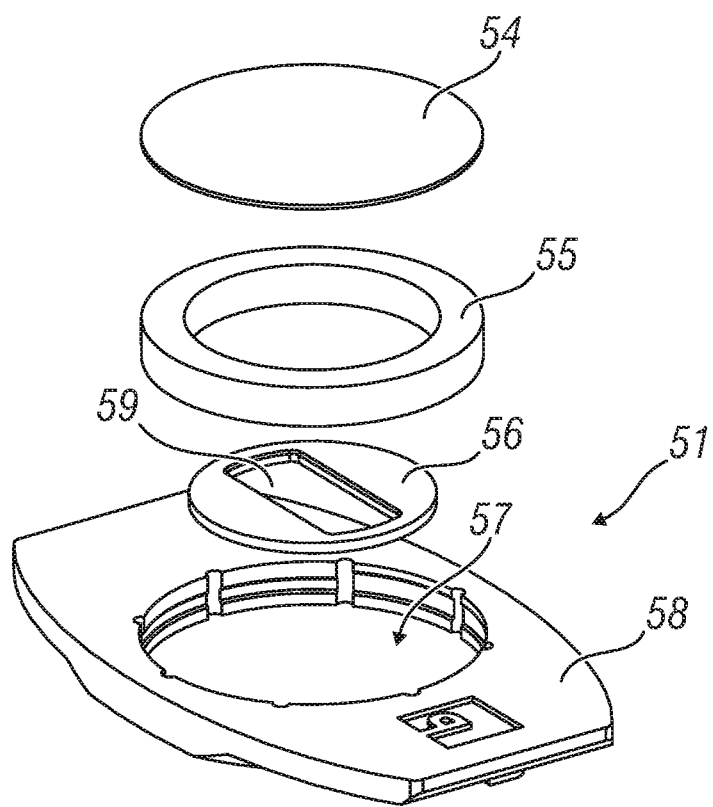
Figure 6:
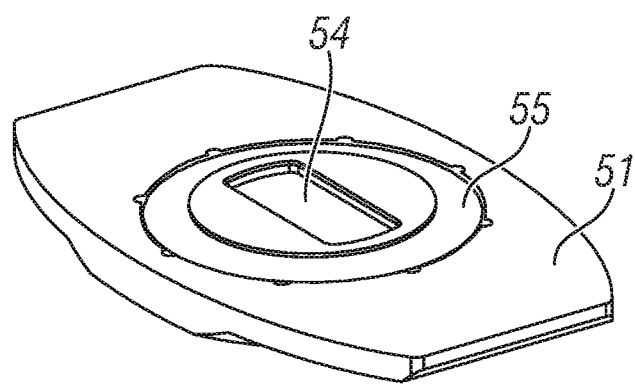

The features and advantages of the present invention will be apparent from the following detailed description of a practical embodiment thereof, illustrated by way of non-limiting example in the accompanying drawings, wherein:

FIG. 1 schematically shows a device for cell culture, with the caps closed, according to the present invention;

FIG. 2 schematically shows a device for cell culture, with the caps open, according to the present invention;

FIG. 3 schematically shows a device for cell culture, viewed from below, according to the present invention;

FIG. 4 schematically shows a device for cell culture, in an exploded view without the caps, according to the present invention;

FIG. 5 schematically shows an exploded view of a cap of a device for cell culture according to the present invention;

FIG. 6 schematically shows a cap of a device for cell culture according to the present invention.

DETAILED DESCRIPTION OF THE INVENTION

With reference to the appended figures, a device 10 for cell culture according to the present invention comprises a rectangular shaped base or main body 11, having a footprint that allow it to be housed in a support of a microscope slide for standard microscopy (e.g.: length from 60 mm to 80 mm, width from 20 to 30 mm, preferably 68 mm in length and 25 mm in width) and, in the case depicted, comprises three chambers 12, 13, and 14.

The main body 11 is recessed so as to have shaped edges 15, 16.

On the short sides of the rectangular main body 11, the edges 15 are continuous, while on the long sides the edges 16 have three pairs of openings 17, 18 and 19 at the respective chambers 12-14. The purpose of the three pairs of openings 17, 18 and 19 is to orient the culture chamber with respect of the inlet and outlet holes of the perfusion fluid produced in the main body, so as to prevent errors during use and they are substantially at the same level as the inner base of the main body 11.

The device 10 comprises three portions, respectively 21-23, preferably cylindrical in shape (alternatively, they could, for example, be oval) that rise from the base of the main body 11 to reach substantially the same level as the lateral edges 16.

The upper surface of each of the three cylinders 21-23 has two through holes, one inlet hole 64-66 and one outlet hole 67-69 of the perfusion.

The three cylinders 21-23 are each surrounded by a circular recess, respectively 24-26.

Each recess 24-26 houses a perforated circular magnet 27 in the shape of a washer, to be compatible with the geometry selected for the chambers 12-14.

The rear of the three cylinders 21-23 are provided with wells 31-33 to reduce the thickness of the main body 11 on the optical path and improve illumination of the sample during transmission optical microscopy.

The rear of the main body 11 is provided, for each chamber, with at least two through holes, exiting from the upper surface of the three cylinders 21-23, an inlet hole 34-36 and an outlet hole 37-39 of the perfusion, which correspond respectively to the inlet holes 64-66 and outlet holes 67-69, positioned on the three cylinders 21-23.

The holes are positioned transversely with respect to the long sides of the main body 11 and are therefore positioned in the same direction as the three pairs of openings 17, 18 and 19.

The rear holes 34-39 have sizes such that they can be connected directly to tubes, by means of gluing, or indirectly by means of metal or plastic connectors-.

The rear of the main body 11 also comprises two pairs of clips 41-43 for each chamber to secure the tubes and prevent stresses on the tube/main body connection during use of the bioreactor.

Each cylinder 21-23 is provided with a corresponding cap 51-53.

Each cap 51-53 comprises at the top a microscopy cover slip 54, for example having a diameter of 12 mm and a thickness of 0.16 mm.

Then, a perforated circular magnet 55 in the shape of a washer, with magnetic poles on the front surface. The magnet 55 has the same size as the magnet 27, and its polarity is oriented so as to attract the magnet 27.

An elastomeric layer 56, having a stiffness, for example, of 40 shore, and with the same size as the inner diameter of the magnet 55, which acts as hydraulic gasket, opposing the three cylinders 21-23.

The elastomeric layer 56 has a through hole 59, preferably rectangular and in any case elongated in shape positioned in the same direction as the three pairs of openings 17, 18 and 19.

The elastomeric layer 56 is secured to the slide 54 by means of adhesive biocompatible or suitable for cell cultures.

The through hole 59 of the elastomeric layer 56 contains the chambers 12-14, housing, either through interference with the elastomer 59 or resting on top of the slide 54, the biological material, such as scaffolds/microstructures/tissues/3D gels or microfluid circuits/functionalized surfaces (2D), to form the culture chamber. In an alternative embodiment, the elastomeric layer 56 does not have the through hole 59. The scaffold or other device is placed on top of the elastomer 56 to produce the culture chamber. Also in this case the culture chamber is associated with the elastomer 56 and is removed together with the cap.

The slide 54, the magnet 55 and the elastomeric layer 56 are housed in a circular hole 57 in the base structure 58 of the cap 51-53 that has an elongated shape. In particular, the shape of the base structure 58 of the cap 51-53 is partially oval (or alternatively rectangular) and its length is the same as the width of the main body 11 (length of short sides) and is such that when the cap is placed on the main body 11 its ends engage in the three pairs of openings 17, 18 and 19. This allows guided alignment of the cap 51-53 and of its components in the desired direction. In particular, it allows alignment of the long side of the chambers 12-14 with the inlet 64-66 and outlet 67-69 perfusion holes.

The caps and the main body thus have a self-aligning geometry, to ensure immediate and correct connection of the perfusion circuit during use, which perfuses in the direction of the chambers.

Moreover, the cap 51-53 has a shape that makes it easy to handle with gloved hands. The main body 11 and the base structure 58 of the cap 51-53 are preferably made of medical grade transparent plastics, for cell cultures, such as PS (polystyrene), COC (cyclic olefin copolymer), PC (polycarbonate), PP (polypropylene), PSU (polysulfone). If the culture chamber only requires to be viewed from above, the main body 11 could also be non-transparent.

The magnets 27 and 55 are preferably made of neodymium iron boron. Alternatively, only one magnet can be used per cap, i.e. a magnetic washer opposed by a ferromagnetic washer. In a further embodiment, the caps can be secured to the base through interference fit. The slide 54 is made of glass.

The elastomeric layer 56 is made with a medical grade elastomer of silicone type, such as polydimethylsiloxane or thermoplastic such as thermoplastic polyurethane (TPE).

All the plastic and elastomeric components have been designed to be produced by injection moulding of plastic materials or other production method applicable on an industrial scale.

The complete bioreactor is then assembled by gluing with medical grade adhesives, or other suitable assembly technique.

The chambers are separate.

The housing is modular both for 3D and 2D cultures, and is integrated in the gasket of the cap.

The solution according to the present invention allows extreme modularity, interchangeability and reduction of the manufacturing and supply costs.

The magnetic closing system, with two opposed magnets with high attraction force (e.g. from 5 N to 20 N, preferably 15 N) facilitates closing and at the same time maintains the hydraulic seal.

The closing system is self-centring between cover and main body and is also self-aligning with respect to the supply channels.

The chamber with raised rigid edge increases the local deformation and consequently the seal of the gasket.

It is possible to use standard Luer connectors, both male and female, at the distal end of the supply tubes, so as to be able to quickly connect the chambers to one another and the bioreactor to different supply systems.

The invention claimed is:

1. A device for cell culture comprising: a main body (11); wherein: said main body (11) comprises a plurality of circular portions (21-23); said device comprises a plurality of caps (51-53); each of said plurality of caps (51-53) comprises a base structure (58) having a circular hole (57), housing an upper slide (54) and an elastomeric layer (56) secured to said slide (54); each elastomeric layer (56) having a rectangular hole (59); said plurality of caps (51-53) being adapted to cooperate with said plurality of circular portions (21-23); and each of said plurality of circular portions (21-23) each comprise an inlet hole (64-66) and an outlet hole (67-69) aligned with a long side of each rectangular hole (59), to perfuse a culture chamber (12-14) located in said rectangular hole (59) of each elastomeric layer (56).

2. The device according to claim 1, characterized in that each rectangular hole (59) is a through hole.

3. The device according to claim 1 characterized in that each of said plurality of caps (51-53) has a base structure (58) of elongated shape.

4. The device according to claim 1, characterized in that said main body (11) is rectangular and comprises edges (15, 16); and in that on long sides of said main body (11), the edges (16) have a plurality of pairs of openings (17, 18, 19) at each culture chamber (12, 14).

5. The device according to claim 1, characterized in that each of said plurality of circular portions (21-23) is surrounded by a circular recess (24-26) housing a circular magnet (27) in the shape of a washer; and each of said plurality of caps (51-53) comprises a circular magnet (55) in the shape of a washer.

6. The device according to claim 1, characterized in that each of said plurality of caps (51-53) engages in pairs of openings (17-19) present in lateral edges (16) of said main body (11).

7. The device according to claim 1, characterized in that each culture chamber is physically separated from an adjacent chamber.

8. The device according to claim 1, characterized in that said elastomeric layer (56) of each cap opposes each of said plurality of circular portions (21-23).

9. The device according to claim 1 characterized in that a rear of the main body (11) is provided with two pairs of clips (41-43) for each of said plurality of circular portions (21-23).

10. A method for producing a device for cell culture according to claim 1 comprising:
 forming the device using injection moulding.

* * * * *